United States Patent [19]

Thomas et al.

[11] 4,349,035
[45] Sep. 14, 1982

[54] BLOOD COLLECTION ASSEMBLY WITH UNIDIRECTIONAL FLOW VALVE

[75] Inventors: Joseph J. Thomas, Bridgewater; Vincent L. Vaillancourt, Livingston, both of N.J.; Marcus J. Millet, New York, N.Y.; William F. Smith, Branchburg, N.J.

[73] Assignee: Johnson & Johnson, New Brunswick, N.J.

[21] Appl. No.: 161,466

[22] Filed: Jun. 19, 1980

Related U.S. Application Data

[62] Division of Ser. No. 886,497, Mar. 14, 1978, abandoned.

[51] Int. Cl.³ .............................................. A61M 1/00
[52] U.S. Cl. ..................................... 128/766; 128/274
[58] Field of Search .......................... 251/149.6, 149.7; 137/318, 322, 843, 846, 850; 141/19, 329, 330; 233/1 A, 26; 128/763, 760, 764, 766, 272, 276, 274, 275, 295; 210/DIG. 23, DIG. 24; 215/247, 311

[56] References Cited

U.S. PATENT DOCUMENTS

| Re. 27,399 | 6/1972 | Urso | 137/850 |
|---|---|---|---|
| 1,066,066 | 7/1913 | Vidy | 251/149.7 |
| 3,159,176 | 12/1964 | Russell et al. | 137/846 |
| 3,355,143 | 11/1967 | Mueller | 251/321 |
| 3,557,778 | 1/1971 | Hughes | 128/2 F |
| 3,570,396 | 3/1971 | Schwartzman | 401/206 |
| 3,659,587 | 5/1972 | Baldwin | 128/2 F |
| 3,734,080 | 5/1973 | Peterson et al. | 128/2 F |
| 3,902,516 | 9/1975 | Rudolph | 137/843 |
| 3,941,149 | 3/1976 | Mittleman | 137/846 |
| 3,957,653 | 5/1976 | Blecher | 128/2 F |
| 3,974,367 | 4/1976 | Ayres | 128/2 F |
| 4,084,606 | 4/1978 | Mittleman | 137/846 |
| 4,134,512 | 1/1979 | Nugent | 128/764 |

OTHER PUBLICATIONS

Anatomy, Descriptive and Surgical, Gray F.R.S., Bounty Books, New York, N.Y. 1977, p. 1081.

*Primary Examiner*—Kyle L. Howell
*Assistant Examiner*—J. L. Kruter

[57] ABSTRACT

A blood collection assembly for receiving a blood sample from a patient but for preventing the blood from flowing out once it has been received. This assembly includes an evacuated receptacle, such as a blood collecting tube, for the reception and retention of a sample of blood. An opening is included in the receptacle into which a penetrable stopper is sealably positioned to maintain the evacuated condition inside the receptacle. Located inside the evacuated receptacle is a unidirectional flow valve through which blood entering the receptacle must pass. When the stopper is penetrated by a sharp cannular instrument carrying blood the pressure on the side of the valve facing the stopper is greater than the pressure in the evacuated receptacle, thereby causing the valve to open so that blood flowing from the instrument flows through the valve and into the receptacle. If the pressure in the receptacle changes so that it is greater than the pressure on the other side of the valve, the valve is operable to close to thereby prevent blood from backflowing into the patient.

1 Claim, 10 Drawing Figures

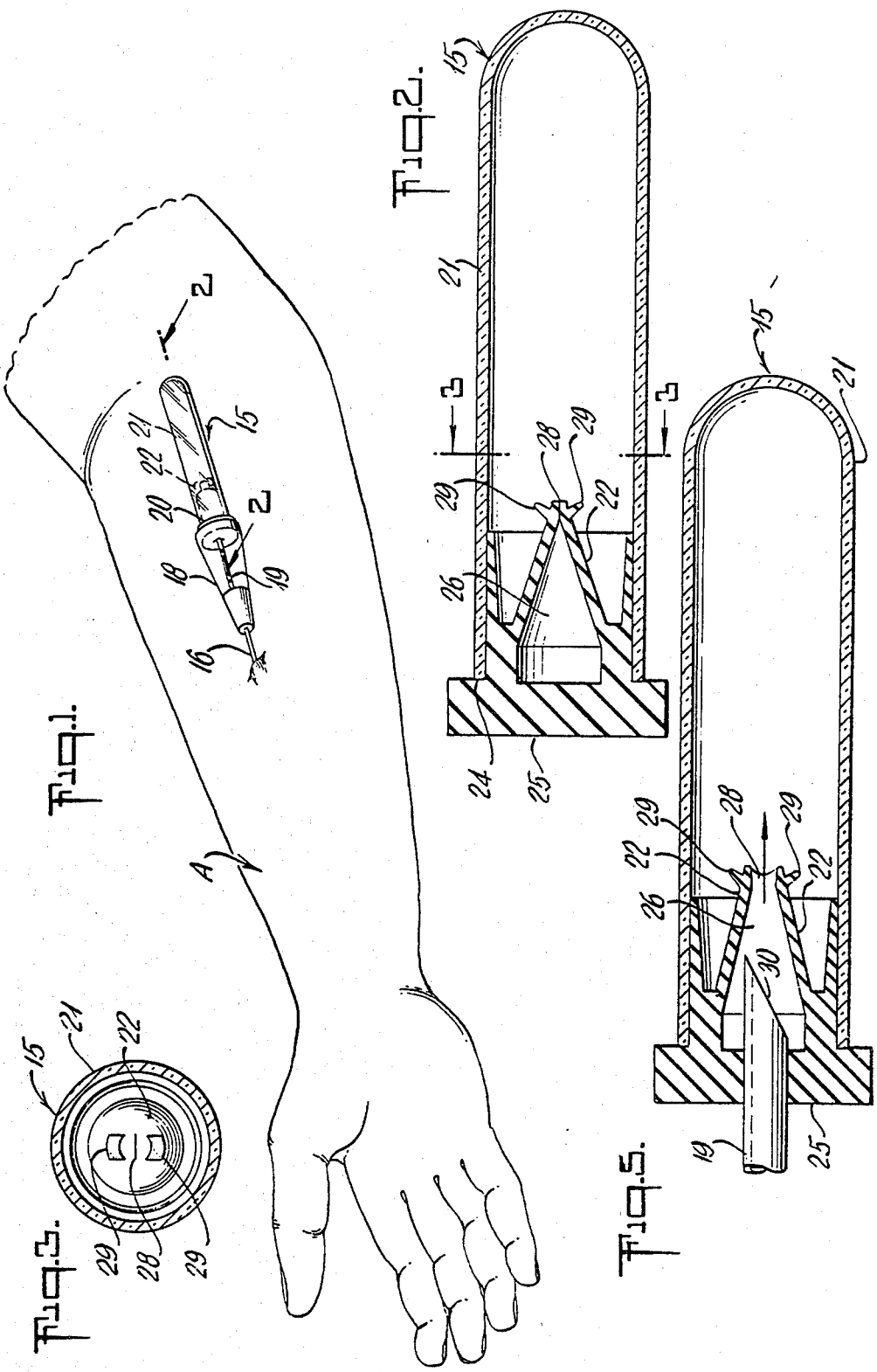

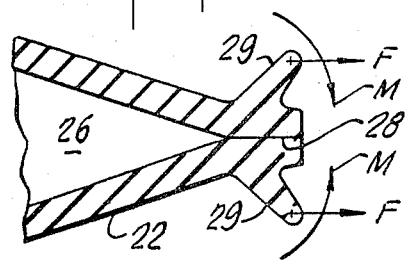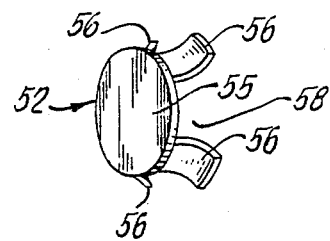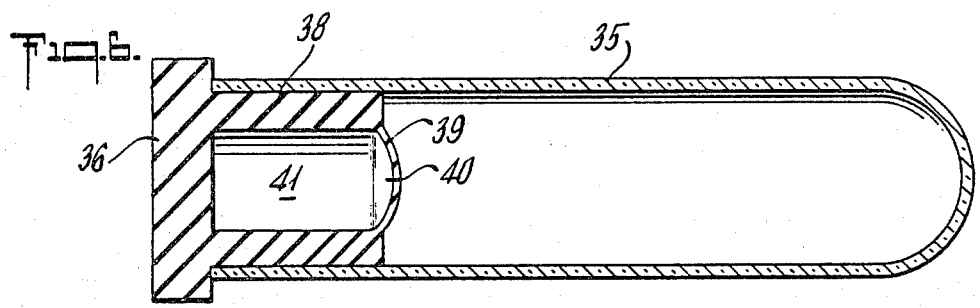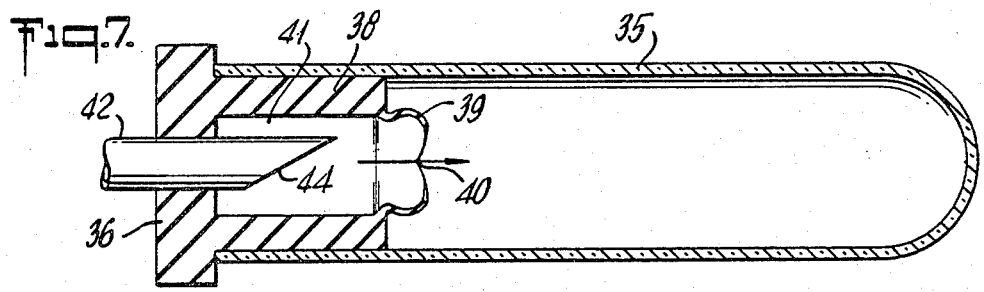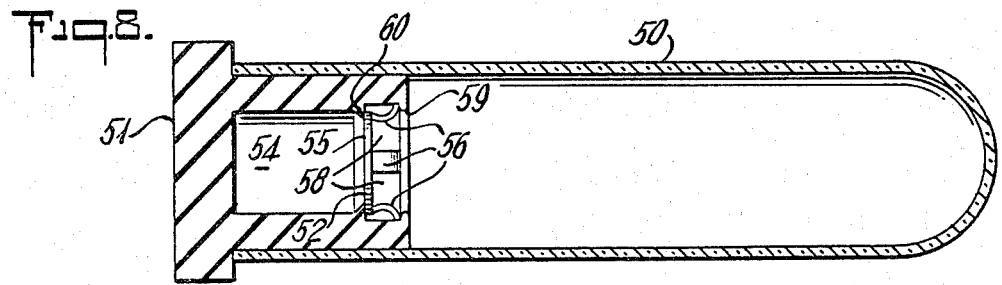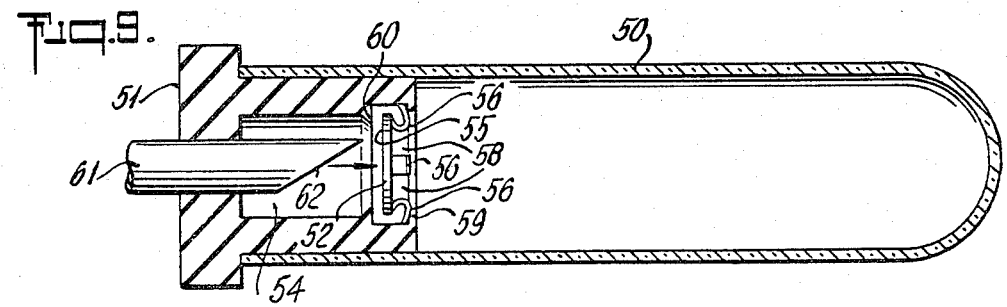

BLOOD COLLECTION ASSEMBLY WITH UNIDIRECTIONAL FLOW VALVE

This is a division of application Ser. No. 886,497, filed Mar. 14, 1978, now abandoned.

BACKGROUND OF THE INVENTION

This invention relates to a blood collection device for receiving a sample of blood from a patient but for preventing the blood from flowing out of the device once it has been received, and more particularly concerns a blood collection assembly with a unidirectional flow valve which is operable to open and close depending upon the pressure gradient on respective sides of the valve and thus control the collection of blood in the device.

Blood samples, for clinical or the like evaluation and testing, are commonly taken from the patient and collected in a suitable collection device such as a glass vial or tube. The blood collecting tube has been evacuated to produce a vacuum therein according to techniques which are conventional in the art. A rubber or similar stopper is provided in the tube so that it can be pierced by a needle on the other end of a similar needle inserted in the patient's vein for taking the sample. Under normal conditions the venous pressure will be greater than the pressure inside the evacuated tube thereby causing the blood to flow from the patient's vein, through the transfer needle system and into the blood collection tube.

Once the sample has been collected in the suitable tube, it is desirable to retain it there and prevent it from backflowing through the needle system and into the patient. Oftentimes the evacuated tube may contain an ingredient for mixture with the incoming blood for purposes of laboratory tests. Should this ingredient backflow into the patient's vein it may produce some unwanted problems. In addition, even though there may be no extra ingredient in the evacuated tube, for sanitary and other purposes it has been found desirable to prevent any backflow of blood from the collection tube. Various techniques are known and used to prevent this backflow of blood from the collection tube. One-way flow valves have been proposed which would operably open and allow the flow of blood to enter the evacuated collection container, but which would operably close to prevent the undesirable backflow of blood toward the patient. Typically, however, a one-way flow valve of this type has been incorporated in the needle assembly which collects the sample of blood from the patient and then deposits the same in the collection tube. The needle assembly of this type includes one or more needles, one end for insertion into the patient's vein, the other end (or other needle) for penetration through the rubber stopper on the collection tube. Somewhere between the two ends of the needle or needles is a one-way flow valve which is operable to allow blood flow through the needle toward the collection tube, but not back toward the patient. Examples of this general type of needle arrangement incorporating a one-way valve are found in U.S. Pat. Nos. 3,874,367; 3,659,587; 3,557,778. Other devices have been proposed wherein the stopper in the collection container is utilized for the one-way control of blood flow. In these devices, the valve is incorporated directly in the stopper or closure of the collection container, preferably in combination with the needle or passageway communicating with the interior of the container. These type valve devices are found in U.S. Pat. Nos. 3,162,195 and 2,551,315.

Placing a one-way valve in the needle or needle assembly as suggested by the above typical references often requires miniaturization and sophisticated designs inasmuch as the area for inclusion of the valve is generally small. This oftentimes increases expense and difficulty of manufacture. Thus, it can be seen that there is room for improvement in incorporating one-way flow valves in blood collection systems.

SUMMARY OF THE INVENTION

The blood collection assembly of the present invention receives a blood sample from a patient but prevents the blood from flowing out once it has been received. This assembly includes an evacuated receptacle for the reception of a sample of blood. Included in the receptacle is an opening into which a penetrable stopper is sealably positioned in order to maintain the evacuated condition inside the receptacle. A unidirectional flow valve through which blood entering the receptacle must pass is located inside the evacuated receptacle. This valve is operable to allow blood to only flow into the receptacle, but not out of the receptacle after the blood has been received therein. During the collection of blood, a sharp cannular instrument carrying blood penetrates the stopper, causing the valve to open so that the blood is passed therethrough and collected inside the receptacle. The valve is closable under the influence of blood flowing out of the receptacle thereby preventing any such backflow of blood into the patient.

In the preferred embodiment of the blood collection assembly of the present invention, the unidirectional flow valve is connected to the stopper inside the receptacle. The valve is positioned apart from the penetrable surface of the stopper to leave a space therebetween for receiving the tip of the sharp cannular instrument which penetrates the stopper for delivery of blood to the receptacle. Elastomeric material, such as rubber, is preferably used to fabricate the stopper. After the stopper is penetrated by the cannular instrument and its tip is received in the space, the valve is operable to open for blood flow into the receptacle, since the pressure in the space is greater than the pressure in the evacuated receptacle. Thus, the positive pressure causes blood to flow into the receptacle. If the pressure in the receptacle equals or exceeds the pressure in the space (or if a negative pressure should develop in the cannular instrument), the valve is operable to close thereby preventing blood from backflowing into the patient. In addition, the valve also closes when the receptacle is virtually full to prevent the undesirable backflow. Various valves, such as elastomeric materials with a slit or like opening therein, may be employed, the slit readily opening to allow blood to flow into the receptacle, but sealably closing to prevent blood from flowing out. It is appreciated that under static conditions inside the receptacle, i.e., the pressure on both sides of the valve being at equilibrium, the valve normally remains closed.

Another aspect of the present invention is the inclusion of a unidirectional flow valve which remains closed inside a receptacle filled with blood during conventional centrifuging operations. This is desirable since oftentimes a small amount of blood will remain trapped inside the valve itself after the blood collection step has been completed. Under normal centrifuging operations, with the stopper placed toward the center of the centrifuge, the centrifugal force on the entrapped blood will urge the valve to open thereby depositing the entrapped blood into the receptacle. In some cases, the different chemical composition of the entrapped blood may cause a change in the composition of the blood which has been affected by reagents, and may adversely affect laboratory results. Accordingly, one embodiment of the unidirectional flow valve incorporates means thereon to maintain the valve closed during centrifuging operations, but which allows the valve to operably open and close during the blood collection steps. When using an elastomeric material with a slit therein for the passage of blood, it is preferable to include an extra mass on each side of the slit so that under centrifugal force each mass produces an inwardly directed moment to keep the slit closed.

From the structural standpoint, the blood collection assembly of the present invention is notably different from prior devices in this field in a number of respects. Primarily, the present blood collection assembly includes a unidirectional flow valve located directly inside the evacuated receptacle so that the valve itself is originally at a vacuum. Being at a vacuum, once the stopper has been penetrated the pressure on that side of the valve is greater than that on the other side of the valve inside the receptacle, causing the valve to open for blood flow. Should the pressure gradient reverse, the valve operably closes to prevent backflow of blood. One of the advantages of including the valve in the receptacle itself, and preferably as a part of the stopper, is that the needle or needle assembly can be more straightforwardly constructed. Instead of positioning the one-way flow valve in the needle assembly as has been previously done, the unidirectional valve is more conveniently, and with greater room for assembly, placed within the evacuated receptacle. Furthermore, placing the unidirectional valve at or near the stopper in the receptacle prevents blood from backflowing into the needle itself if a negative pressure should develop therein. In the previous devices known to this art, blood may backflow into the needle before encountering the valve which prevents it from further travel either in that needle or to the needle inserted in the patient's vein. It can be seen that the structure of the blood collection assembly of this invention not only provides a means to prevent backflow of blood into the patient, but offers advantages over the previous blood collection devices as well.

BRIEF DESCRIPTION OF THE DRAWINGS

FIG. 1 is a perspective view illustrating a sample of blood being collected from a patient utilizing the preferred blood collection assembly of the present invention;

FIG. 2 is a cross-sectional view taken along lines 2—2 of FIG. 1;

FIG. 3 is a cross-sectional view taken along lines 3—3 of FIG. 2;

FIG. 4 is an enlarged partial plan view of the unidirectional flow valve illustrated in the embodiment of FIG. 2;

FIG. 5 is a cross-sectional view illustrating the unidirectional valve of FIG. 2 in the open position for allowing a blood sample to pass therethrough;

FIG. 6 is a cross-sectional view illustrating another embodiment of the unidirectional flow valve in the closed position;

FIG. 7 is a cross-sectional view illustrating the unidirectional flow valve of FIG. 6 in an open position;

FIG. 8 is a cross-sectional view illustrating a further embodiment of the unidirectional flow valve in the closed position;

FIG. 9 is a cross-sectional view illustrating the valve of FIG. 8 in the open position; and FIG. 10 is an enlarged perspective view illustrating the construction of the unidirectional flow valve of FIGS. 8 and 9.

DETAILED DESCRIPTION

While this invention is satisfied by embodiments in many different forms there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Adverting to the drawings, particularly to FIG. 1, there is illustrated the blood collection assembly 15 of the present invention shown during the collection of a blood sample from the arm A of a patient. A needle 16, projecting from a hub device 18, is inserted in the patient's vein so that the blood sample can be withdrawn. Inside hub 18 and communicating with needle 16 is a second needle or cannula 19 which has a sharp end facing in the opposite direction. Blood collection assembly 15 is inserted into hub 18 with a penetrable stopper 20 in the blood collection assembly being inserted first. Cannula 19 pierces stopper 20 as the blood collection assembly is pushed farther into hub 18. Blood then flows through cannula 19 into a receptacle 21 such as a glass vial or the like. A unidirectional flow valve 22 is located near stopper 20 so that blood is allowed to flow into receptacle 21 when valve 22 is open, but is prevented from flowing out of receptacle 21 by the closing action of valve 22 if such backflow occurs.

Turning now to FIGS. 2 and 3, receptacle 21 may be any suitable blood collection container, including glass vials and the like, which are known and conventional in this field. Receptacle 21 is generally tubular in shape, and somewhat elongated so as to hold a sufficient quantity of blood for sampling purposes. Receptacle 21 generally has only one opening 24 therein so that the blood sample can be passed into the inside of the receptacle. Inserted in opening 24 is a stopper 25, which is fabricated to be penetrable by a sharp instrument and is positioned in opening 24 to provide a tight seal. This type seal is required since the receptacle 21 is evacuated so that the inside thereof is substantially at a vacuum. This, of course, facilitates the flow of blood into the receptacle since the pressure outside receptacle 21 is greater than the pressure inside the receptacle in an amount sufficient to cause blood to flow in that direction. Accordingly, stopper 25 is fit in opening 24 to maintain the evacuated condition inside receptacle 21. To facilitate penetrability, stopper 25 is generally fabricated from an elastomeric material, such as rubber, whether natural or synthetic. The elastomeric material also serves to provide a tight seal around the sharp instrument which penetrates the stopper thereby preventing any blood from flowing around the outside surface of the sharp instrument, and also preventing an unnecessarily large opening in the stopper, caused by the penetration, which may induce unnecessarily large pressure gradients across the receptacle inasmuch as it is evacuated. Thus, with the stopper in position, the pressure inside receptacle 21 is less than normal atmospheric pressure outside the receptacle so that the proper pressure gradient can be established to cause blood to flow into the receptacle after stopper 25 has been penetrated.

Connected to stopper 25, and in this instance integrally formed or molded therewith, is unidirectional flow valve 22. It is appreciated that valve 22 may just as conveniently be a separate piece, insertable into either stopper 25 or inside receptacle 21 near the stopper. The purpose of valve 22 is to operably open to allow blood to only flow into receptacle 21, but to operably close to prevent blood from backflowing out of the receptacle 21 toward the patient. As seen in FIGS. 2 and 3, valve 22 is an elastomeric material, such as rubber, which is substantially tubular in cross-section and which projects from stopper 25 a short distance into receptacle 21. At the far or distal end of valve 22, it tapers to a point. Thus, between the penetrable surface of stopper 25 and the point of valve 22 there is a space 26 which is designed to receive the tip of cannula 19 for delivering blood to the receptacle as will hereinafter be discussed. At the point of the tubular valve is a slit 28 which communicates with space 26. This slit serves as an operable passageway to open up to allow blood to flow into receptacle 21; when slit 28 is closed, it forms a liquid tight seal so as to prevent blood from flowing therethrough in that closed position. Being elastomeric, valve 22 with its slit 28 therein readily functions under the pressure gradients involved in delivering blood into the receptacle to open and to close when necessary. It is appreciated that under static conditions, i.e., when the pressure on both sides of the slit is substantially at equilibrium, the slit remains closed to provide the tight seal referred to above. It is also pointed out that other configurations in this type valve may be employed, for example, a dome-shaped valve with an operable hole therein which is capable of opening under positive pressure and sealably closing under negative pressure. In the instance of a dome-type valve, the space between the penetrable surface of the stopper and the operable opening is substantially spherically shaped.

Referring to FIG. 4 in combination with FIG. 2, it can be seen that there are two masses 29, one on each side of valve 22 near slit 29. These masses 29 are integrally formed, in the elastomeric embodiment, in the valve, and are spaced a short distance inwardly on respective sides of the valve from the distal end or point thereof. The purpose of these masses is to maintain the slit 28 in a closed position during conventional centrifuging operations. In those operations the blood filled tube is inserted in the apparatus so that the stopper faces toward the center of the centrifuge. If any blood is entrapped in space 26 after valve 22 closes during the blood collection step, the centrifugal force, acting on that entrapped blood may cause it to force open the valve with the entrapped blood passing through slit 28 into the receptacle. This may be undesirable inasmuch as the entrapped blood may have a different chemical composition than the blood in the receptacle which may be affected by reagents or chemical ingredients. To prevent this occurrence, masses 29 are so positioned so that the centrifugal force, designated as F in FIG. 4, acts in the direction shown. Concurrently, force F produces an inwardly directed moment M on each side of valve 22 thereby urging the respective sides of the slit toward each other and thus maintaining the slit in a sealably closed condition. It is appreciated that masses 29, while serving as an effective closure expedient during centrifuge operations, do not interfere with the normal opening and closing function of valve 22 during the collection of a blood sample from a patient. Moreover, while it may be preferable to include masses 29 on this type of valve, the extra masses may just as conveniently be omitted, if desired.

FIG. 5 depicts the operation of unidirectional flow valve 22 during the collection of the sample of blood. Before sharp cannula 19, which carries blood from the patient's vein, enters penetrable stopper 25, both the space 26 and the remainder of the inside of receptacle 21 are at the evacuated pressure level. Thus, slit 28 is in the closed position. As soon as cannula 19 penetrates stopper 25 so that its tip 30 is positioned in space 26, there is a pressure gradient established. The venous pressure from the patient being greater than the evacuated condition in the receptacle causes the blood to flow from cannula 19 toward the receptacle. In addition, space 26 becomes an upstream portion in the receptacle, with the remainder of the receptacle, on the other side of the slit, being the downstream portion of the receptacle. This gradient between upstream and downstream portions on opposite sides of the valve is sufficient to operably open slit 28 to thereby permit blood to flow into receptacle 21. When receptacle 21 is almost full, valve 22, and particularly slit 28, closes thereby preventing any backflow of blood received in the receptacle. Should a negative pressure develop in cannula 19 (or needle 16 inserted in the patient's vein), this tends to further close off the valve thereby reinforcing the already sealed valve in the blood filled receptacle. It is understood that anytime the pressure in receptacle 21 equals or exceeds the pressure in space 26, from any prevailing circumstances, slit 28 in the valve is operably closed so that blood is prevented from backflowing out of the receptacle. If can also be seen in FIG. 5 that the position of valve 22 prevents any blood from backflowing into cannula 19, which is one of the advantages of this invention. This is especially advantageous if receptacle 21 includes extra ingredients for the laboratory testing of the blood sample. With the receptacle full and the blood collection step completed, cannula 19 is withdrawn from stopper 25 which preferably is sufficiently resilient to sealably close the penetration hole made by cannula 19. This assists in maintaining the integrity of the sample of collected blood.

Another embodiment of a unidirectional flow valve is illustrated in FIGS. 6 and 7. A suitable receptacle, such as a glass vial 35, is plugged by a stopper 36, both the receptacle and the stopper being similar to the corresponding elements described in the above embodiment. In this instance, however, integral with stopper 36 is a stretchable elastomeric unidirectional flow valve 38. A portion of valve 38 has a thin, stretchable balloon-like membrane 39 with a pre-punctured opening 40 which prevents the passage of blood therethrough in its relaxed state, thereby providing the closed position of the valve. Once again, as in the above embodiment, a space 41 is provided between the penetrable surface of stopper 36 and balloon-like member 39. Space 41 is adapted to receive the tip of a sharp cannula instrument. In FIG. 7, cannula 42 has penetrated stopper 36 so that its tip 44 lies in space 41. By so penetrating, the pressure in space 41 becomes positive due to the venous pressure inside cannula 42. Inasmuch as receptacle 35 has been evacuated to produce a vacuum, the pressure gradient between space 41 and receptacle 35 acts on ballon membrane 39 to enlarge or blow up that membrane and thereby open prepunctured opening 40. With opening 40 in this condition, a channel is provided for the flow of blood into receptacle 35. After cannula 42 is withdrawn from the blood filled receptacle, the pressures on each side of membrane 39 tend to equalize, thereby shrinking the expanded membrane so that the pre-punctured opening again seals itself closed. It is appreciated that the actual configurations of this type of valve may vary according to choice of the designer as long as the above functions are effectively accomplished.

Still another embodiment of a unidirectional flow valve for incorporation in the blood collection assembly of the present invention is illustrated in FIGS. 8–10. An evacuated receptacle 50, similar to the previous embodiments, is provided with a penetrable stopper 51 which sealably maintains the evacuated condition inside the receptacle. Stopper 51 has a portion extending into the receptacle at the end of which a resiliently operable unidirectional flow valve 52 is positioned. A space 54 is left between the penetrable surface of stopper 51 and valve 52 so that the tip of the sharp cannula instrument can be received therein. As more clearly seen in FIG. 10, valve 52 includes a substantially flat sealing surface 55 which, in this instance is circularly shaped for compatibility with the circular shape of stopper 51. Projecting substantially downwardly or away from sealing surface 55 are a plurality of legs 56 which are resiliently flexible in spring-like fashion. The curvature of legs 56 assists in providing them with this spring component as they support sealing surface 55. In addition, legs 56 are spaced apart from each other to leave gaps 58 therebetween.

Resiliently operable valve 52 is positioned at the end of stopper 51 so that the free ends of its legs 56 are secured to an undercut 59 at the end of stopper 51. This undercut serves as a platform or support base for the resilient functioning of the valve. Spaced inwardly from the end of stopper 51 is a valve seat 60 which is essentially a protuberance projecting radially inwardly. This valve seat is spaced from undercut 59 so that, in assemblying valve 52 therein, legs 56 must be compressed so that sealing surface 55 contacts valve seat 60 in order to provide an effective closure. Thus, under equilibrium pressure conditions on both sides of valve 52 this position represents the closed condition of the unidirectional flow valve.

In FIG. 9, a sharp cannula 61 carrying blood has penetrated stopper 51 so that its tip 62 is positioned in space 54. The venous pressure on the other end of cannula 61, being greater than the vacuum inside evacuated receptacle 50, causes a pressure gradient. When the pressure inside space 54 exceeds the pressure inside of receptacle 50 by an amount sufficient to overcome the resistance of spring legs 56 (the "opening pressure"), sealing surface 55 is forced away from valve seat 60. Thus, blood then flows around sealing surface 55 and through gaps 58 between spring legs 56 and then on into the inside of receptacle 50. It is appreciated that the positive pressure acting against valve 52 causes a further compression of spring legs 56 which in turn moves sealing surface 55 away from valve seat 60 so that flow of blood is permitted. If the pressure inside receptacle 50 becomes equal to or exceeds the pressure inside space 54 (with a slight accountability for the "opening pressure" spring leg resistance), legs 56 are released from the further compression thereby urging sealing surface 55 back into contact with valve seat 60 to prevent blood from backflowing into space 54 or onto the patient.

A valve of the type illustrated in FIGS. 8–10 may be fabricated from many materials which are inherently resilient or to which resiliency may be imparted. While this resilient valve is preferably made of a thermoplastic material which does not adversely affect blood, such as polycarbonate or polystyrene, it may also be made of a metal such as stainless steel.

Thus, there has been provided a blood collection assembly for receiving a blood sample from a patient but for preventing the blood from flowing out once it has been received which includes a unidirectional flow valve located inside an evacuated receptacle for retaining the blood sample. It is apparent that the blood collection assembly of the within invention fully satisfies the aims, advantages and aspects as set forth above.

What is claimed is:

1. A blood collection assembly for receiving a blood sample from a patient, but for preventing the blood from flowing out once it has been received comprising:
   a receptacle for the reception and retention of a sample of blood having a longitudinal axis;
   said receptacle having an inside pressure less than normal atmospheric pressure outside said receptacle thereby establishing a pressure gradient across said receptacle,
   said receptacle including an opening therein;
   a penetrable stopper sealably positioned in said opening to maintain said pressure gradient across said receptacle; and,
   a unidirecitonal flow-valve means disposed on said stopper inside said receptacle through which blood entering said receptacle must pass,
   said valve means spaced apart from the penetrable surface of said stopper and defining between said valve means and said penetrable surface, a chamber for receiving a tip of a sharp cannula instrument, and defining between said valve means and the interior of said receptacle a downstream portion;
   said valve means adapted to open for blood flow in response to the introduction of the tip of said cannula instrument into said chamber through said penetrable stopper, the pressure of said upstream portion being greater than said downstream portion following said penetration, and said valve means adapted to close if the pressure of said downstream portion equals or exceeds the pressure of said upstream portion;
   wherein said flow valve means includes an annular flange disposed on said stopper in said chamber defining a valve seat;
   a resiliently operable valve member disposed in said chamber downstream of said valve seat, said valve member remaining sealably closed against said valve seat when the pressure in said receptacle equals or exceeds the pressure in said chamber, said valve member being resiliently flexible to move away from said valve seat when the pressure in said chamber is greater than the pressure in the remainder of said receptacle thereby allowing blood to flow into said receptacle;
   wherein said valve member includes a substantially flat sealing surface substantially perpendicular to the longitudinal axis for contact with said valve seat and a plurality of spaced apart concave spring legs deformable toward the stream axis projecting substantially downstream from said sealing surface to serve as resilient supports for the same, the free ends of said legs being secured to said stopper so that the sealing surface engages said valve seat when said legs are under spring compression, whereby when the pressure in the space is greater than the pressure inside the receptacle said spring legs are urged under further compression to move said sealing surface away from said valve seat so that blood flows in the gaps between the spaced apart legs into the receptacle, and when the pressure inside the receptacle equals or exceeds the pressure inside the chamber, said legs are released from said further compression thereby urging said sealing surface back into contact with said valve seat to prevent blood from backflowing into said chamber.

* * * * *